United States Patent [19]

Clitherow

[11] 4,399,293

[45] Aug. 16, 1983

[54] PROCESS FOR THE PREPARATION OF A FURAN DERIVATIVE

[75] Inventor: John W. Clitherow, Sawbridgeworth, England

[73] Assignee: Glaxo Group Limited, London, England

[21] Appl. No.: 350,414

[22] Filed: Feb. 19, 1982

[30] Foreign Application Priority Data

Feb. 20, 1981 [GB] United Kingdom ............... 8105454

[51] Int. Cl.³ .......................................... C07D 307/52
[52] U.S. Cl. ................................................. 549/494
[58] Field of Search ....................................... 549/494

[56] References Cited

U.S. PATENT DOCUMENTS 4,128,658 12/1978 Price et al. ..................... 424/285

OTHER PUBLICATIONS

Toso et al., Gazzetta Chimica Italiana, vol. 110 (1980), pp. 345–350.

*Primary Examiner*—Richard Raymond
*Attorney, Agent, or Firm*—Bacon & Thomas

[57] ABSTRACT

Ranitidine is prepared by reacting a compound of formula (II)

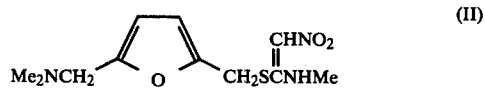

(II)

with aziridine. The reaction may be carried out in the absence of a solvent or preferably in the presence of a solvent such as water or an alkanol at elevated temperature.

8 Claims, No Drawings

PROCESS FOR THE PREPARATION OF A FURAN DERIVATIVE

This invention relates to a process for the preparation of a furan derivative.

The furan derivative of formula (I)

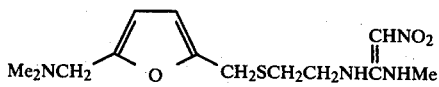
(I)

which is known as ranitidine is disclosed in British Patent Specification No. 1565966 as a potent and selective $H_2$-antagonist.

The present invention provides a process for the preparation of raniditine of formula (I) which comprises reacting a compounds of formula (II)

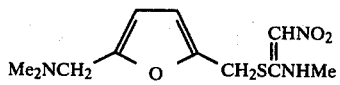
(II)

with aziridine.

The reaction may be carried out in the absence or preferably in the presence of a suitable solvent, for example water, dimethylformamide, an ether e.g. tetrahydrofuran, or an alkanol, e.g. methanol or ethanol. The reaction is conveniently carried out at a temperature in the range of 20° to 100° C., preferably at an elevated temperature, e.g. 60° to 100° C.

The process provides a novel and useful method for the preparation of the compound ranitidine and has the advantage that the evolution of a thiol is eliminated. Since it is necessary to prevent the release of such thiols into the environment and this requires the use of specialised equipment which is expensive to run, a process which does not involve the evolution of a thiol offers a significant advantage.

The intermediate of formula (II), namely 1-[[5-[(dimethylamino)methyl]-2-furanylmethyl]thio]-N-methyl-2-nitroethenamine, is a novel compound and forms part of the present invention. A futher advantage of the process according to the invention is that the compound of formula (II) can be readily produced in pure crystalline form.

The compound of formula (II) may be prepared by reaction of a thiol of formula (III)

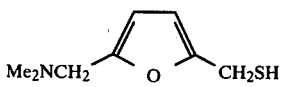
(III)

with a nitrovinyl derivative of formula (IV)

(IV)

where L is a leaving group such as alkylthio, e.g. methylthio. The reaction is preferably carried out at room temperature, in the presence of a solvent, e.g. water, tetrahydrofuran or an alkanol e.g. methanol, and in an inert atmosphere, for example under nitrogen. If desired the compound of formula (II) may be isolated and used as an acid addition salt, e.g. oxalate or hydrochloride.

The thiol (III) may be used directly or is generated in situ from an acid addition salt such as an oxalate salt (1:1) by treatment with a base e.g. aqueous potassium hydroxide.

The intermediate (III) may be prepared as described in British Patent No. 2067991A.

If desired the furan derivative of formula (I) once obtained may be converted into an acid addition salt, e.g. a hydrochloride, using conventional methods. Thus for example appropriate quantities of the free base of formula (I) and an acid, e.g. hydrochloric acid, may be mixed in a suitable solvent(s), e.g. an alcohol such as ethanol, or an ester such as ethyl acetate.

The invention is illustrated by the following Preparation and Examples:

Preparation

1-[[5-[(Dimethylamino)methyl]-2-furanylmethyl]thio]-N-methyl-2-nitroethenamine

To a stirred mixture of 5-[(dimethylamino)methyl]-2-furanmethanethiol oxalate (1:1) (2.61 g) and N-methyl-(1-methylthio)-2-nitroethenamine (1.48 g) in water (10 ml) at room temperature under a nitrogen atmosphere was added a solution of potassium hydroxide (1.12 g) in water (2 ml). After 5 h, the solid was filtered off, washed with water and dried to give the title compound (2.20 g) m.p. 101°–103°. A sample crystallised from ethanol had m.p. 100°–102°.

Found: C, 48.4; H, 6.3; N, 15.2; $C_{11}H_{17}N_3O_3S$ requires: C, 48.7; H, 6.3; N, 15.5%

EXAMPLE 1

N-[2-[[5-[(Dimethylamino)methyl]-2-furanylmethyl]thio]ethyl]-N'-methyl-2-nitro-1,1-ethenediamine A mixture of 1-[[5-[(dimethylamino)methyl]-2-furanylmethyl]thio]-N-methyl-2-nitroethenamine (1.2 g) and aziridine (0.25 g) in water (2 ml) was heated at 98°–100° with stirring until the solid has dissolved. After heating for a further 10 min., the solution was evaporated in vacuo. The oily residue was chromatographed (silica/methanol—0.88 ammonia 79:1) and the appropriate eluate evaporated in vacuo to give an oil (0.89 g). This was dissolved in 4-methylpentan-2-one (3 ml) and the solid which separated was filtered off, washed with 4-methylpentan-2-one and isopropyl acetate and dried to give the title compound (0.61 g), m.p. 66.5°–68°, which was not depressed on admixture with a sample prepared according to the method of Example 15 in British Pat. No. 1565966.

EXAMPLE 2

N-[2-[[5-[(Dimethylamino)methyl]-2-furanylmethyl]thio]ethyl]-N'-methyl-2-nitro-1,1-ethenediamine A mixture of 1-[[5-[(dimethylamino)methyl]-2-furanylmethyl]thio]-N-methyl-2-nitroethenamine (1.2 g), and aziridine (0.25 g) in ethanol (3 ml) was heated at reflux on a steam-bath for 0.5 h. The brown solution was evaporated in vacuo. The oily residue was chromatographed (silica/methanol-0.88 ammonia 79:1), and the appropriate eluate was evaporated in vacuo to give a yellow oil (0.85 g). This oil was dissolved in hot 4-methylpentan-2-one (3 ml). The solution was cooled to precipitate out the title compound (0.52 g) which had an n.m.r. identical to that of the product of the above example.

EXAMPLE 3

N-[2-[[5-[(Dimethylamino)methyl]-2-furanylmethyl]thio]ethyl]-N'-methyl-2-nitro-1,1-ethenediamine A mixture of 1-[[5-[(dimethylamino)methyl]-2-furanylmethyl]thio]-N-methyl-2-nitroethenamine (0.27 g) and aziridine (0.1 g) was heated at 98°–100° for 3 minutes to give a pale brown oil consisting of the title compound. T.l.c. silica/methanol-0.88 ammonia (79:1) $R_f$ 0.45, consistent with that prepared according to the method of Example 15 in British Pat. No. 1565966.

I claim:

1. A process for the preparation of ranitidine of formula (I)

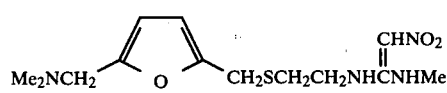

which comprises reacting a compound of formula (II)

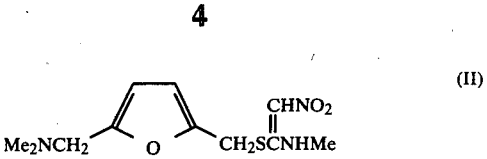

with aziridine.

2. A process as claimed in claim 1 carried out in the presence of a suitable solvent.

3. A process as claimed in claim 3 in which the solvent is water or an alkanol.

4. A process as claimed in claim 1 carried out at a temperature in the range 20° to 100° C.

5. A process as claimed in claim 1 carried out at a temperature in the range 60° to 100° C.

6. A process as claimed in claim 1 in which the compounds of formula (I) is converted into an acid addition salt.

7. A process as claimed in claim 6 in which the acid addition salt is the hydrochloride.

8. The compound 1-[[5-[(dimethylamino)methyl]-2-furanylmethyl]thio]-N-methyl-2-nitroethenamine of formula (II)

Me₂NCH₂—[furan]—CH₂SCNHMe, CHNO₂ (II)

* * * * *